US00PP30969P2

(12) United States Plant Patent
Clark

(10) Patent No.: US PP30,969 P2
(45) Date of Patent: Oct. 22, 2019

(54) ***COLEUS* PLANT NAMED 'UF15-20-6'**

(50) Latin Name: *Plectranthus scutellarioides*
Varietal Denomination: UF15-20-6

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 16/350,113

(22) Filed: Sep. 26, 2018

(51) Int. Cl.
*A01H 5/00* (2018.01)
*A01H 6/50* (2018.01)

(52) U.S. Cl.
USPC ..... Plt./373

(58) Field of Classification Search
USPC ..... Plt./373
CPC ..... A01H 5/00; A01H 6/50
See application file for complete search history.

(56) References Cited

U.S. PATENT DOCUMENTS

PP28,566 P2 10/2017 Clark et al.

OTHER PUBLICATIONS

U.S. Appl. No. 15/732,775, filed Dec. 27, 2017, Clark.
U.S. Appl. No. 15/732,774, filed Dec. 27, 2017, Clark.
U.S. Appl. No. 15/732,779, filed Dec. 27, 2017, Clark.
U.S. Appl. No. 15/732,777, filed Dec. 27, 2017, Clark.
U.S. Appl. No. 15/732,776, filed Dec. 27, 2017, Clark.
U.S. Appl. No. 15/732,778, filed Dec. 27, 2017, Clark.
U.S. Appl. No. 16/350,116, filed Sep. 26, 2018, Clark.
U.S. Appl. No. 16/350,114, filed Sep. 26, 2018, Clark.
Variety specific information as indicated in transmittal letter Information Disclosure Statement for U.S. Appl. No. 16/350,113, filed Mar. 26, 2019.

*Primary Examiner* — Annette H Para
(74) *Attorney, Agent, or Firm* — Dentons US LLP

(57) ABSTRACT

'UF15-20-6' is a new *Coleus* plant with novel characteristics that include excellent heat tolerance, distinct, highly lobed leaves that display a unique and consistent green, pink, and white coloration pattern, and a vigorous, compact upright growth habit and excellent lateral branching. 'UF15-20-6' exhibits superior foliage color stability when grown under all conditions, including both sun and shade conditions. Further, 'UF15-20-6' exhibits long-season performance until late fall.

3 Drawing Sheets

Latin name of the genus and species of the plant claimed: *Plectranthus scutellarioides.*

Cultivar denomination: 'UF15-20-6'.

BACKGROUND OF THE INVENTION

The invention relates to a new and distinct cultivar of *Coleus* plant that has been designated 'UF15-20-6'. This cultivar originated from an open pollination between the female *Coleus* plant 'UF14-14-8' (unpatented) and an unknown male *Coleus* plant. This open pollination was conducted in Gainesville, Fla. from May through November of 2014. Asexual propagation of 'UF15-20-6' first occurred in Gainesville, Fla. in May of 2015 using meristem tip cuttings. That and all subsequent asexual propagations of 'UF15-20-6' have remained true-to-type and retained the distinctive features of this novel cultivar.

SUMMARY OF THE INVENTION

The following are the most outstanding and distinguishing characteristics of 'UF15-20-6' when grown in Gainesville, Fla. under typical horticultural practices. 'UF15-20-6' exhibits excellent heat tolerance and distinct, highly lobed leaves that display a unique and consistent green, pink, and white coloration pattern. 'UF15-20-6' exhibits superior foliage color stability when grown under all conditions, including both sun and shade conditions. In particular, white leaf coloration like that exhibited by 'UF15-20-6' will burn in full sun or fade in the shade; however, 'UF15-20-6' is unique in that well-defined zones of green, pink, and white coloration are retained in both shade and full sun. 'UF15-20-6' also exhibits a vigorous, compact upright growth habit and excellent lateral branching, and thus provides ample vegetative propagules for producers when utilized as a stock plant. Further, 'UF15-20-6' exhibited long-season performance until late fall in landscape trials that were conducted in Gainesville, Fla.

'UF15-20-6' can be distinguished from its female parent, 'UF14-14-8', at least based upon leaf shape, leaf coloration, and plant growth habit. Unlike the larger leaves of 'UF14-14-8', the leaves of 'UF15-20-6' are highly lobed. Also, the leaves of 'UF15-20-6' display a distinct green, pink, and white coloration pattern that is further distinguished by a pronounced purple pinstripe around the leaf margin; whereas, the leaves of 'UF14-14-8' display a bright pink, maroon, and lime green coloration pattern. Further, 'UF15-20-6' exhibits a robust, well-branched upright habit, which can be easily distinguished from the more vigorous, more upright habit and less lateral branching of 'UF14-14-8'.

BRIEF DESCRIPTION OF THE DRAWINGS

This new *Coleus* plant is illustrated by the accompanying photographs, which show the plant's form and foliage. The colors shown are as true as can be reasonably obtained by conventional photographic procedures. The photographs in FIGS. 2 and 3 are of plants that were grown from unrooted cuttings in a poly-covered plastic greenhouse in Gainesville, Fla. for 11 weeks from November, 2017 through February, 2018.

DETAILED BOTANICAL DESCRIPTION

Figure 1:
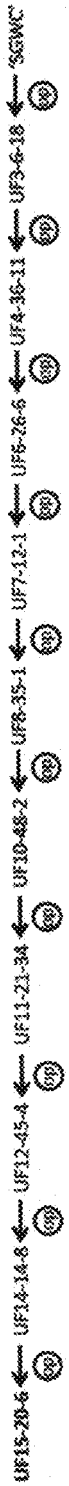
FIG. 1—Shows the pedigree of 'UF15-20-6'.
Figure 2:
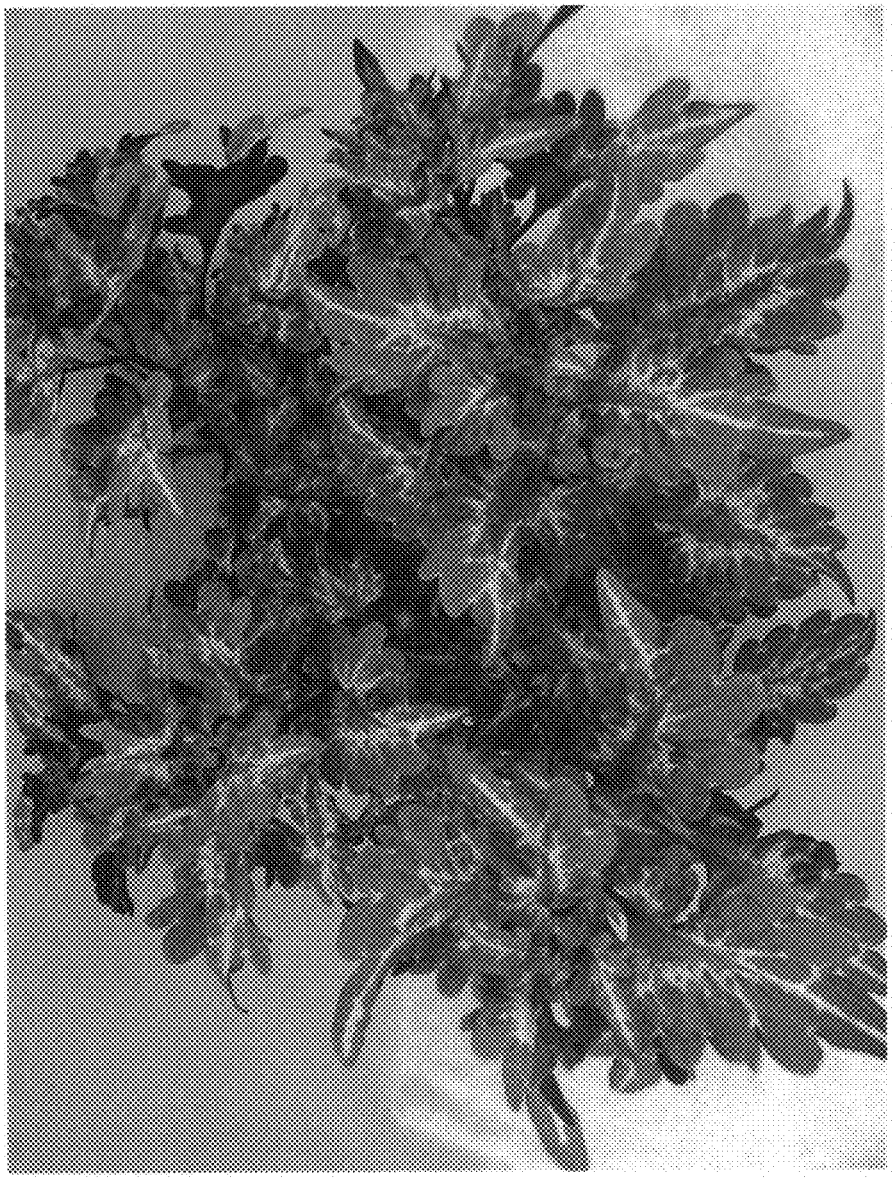
FIG. 2—Shows the growth habit, form, and foliage of 'UF15-20-6'.
Figure 3:
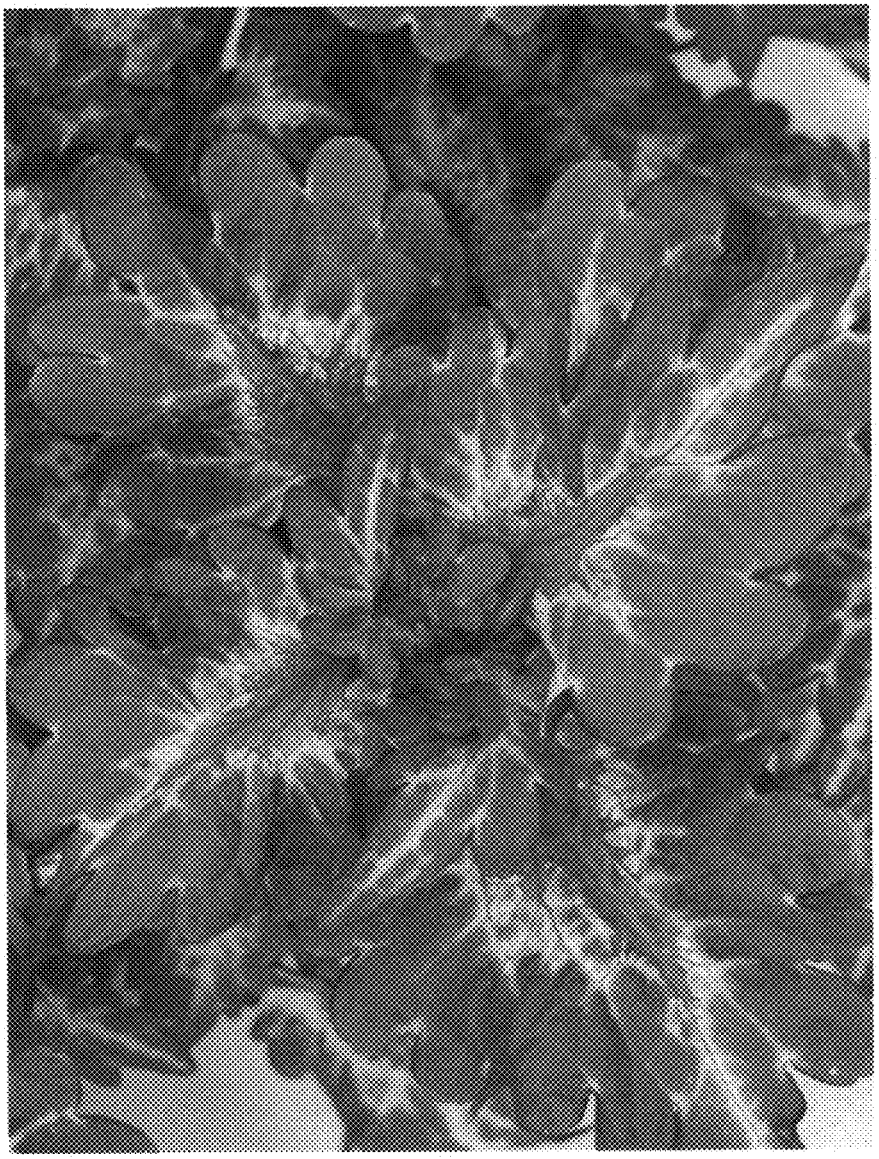
FIG. 3—Shows a close-up of the foliage of 'UF15-20-6'.

The following detailed description sets forth the distinctive characteristics of 'UF15-20-6'. The detailed description was obtained using 10-week-old plants grown from unrooted cuttings during November, 2017 through February, 2018 in a poly-covered plastic greenhouse in Gainesville, Fla. The plants were propagated in mist for 10 days after cuttings were stuck, and then they were grown in 1-gallon pots for approximately 9 weeks. Color references are to The R.H.S. Colour Chart of The Royal Horticultural Society of London (R.H.S.), 2007 5th Edition.

Classification:

*Family*.—Lamiaceae.

*Botanical*.—*Plectranthus scutellarioides*.

*Common name*.—*Coleus*.

*Cultivar name*.—'UF15-20-6'.

Plant description:

*Form*.—Spreading.

*Habit*.—Upright.

*Height* (*from top of soil*).—30-35 cm.

*Width* (*horizontal plant diameter*).—50-55 cm.

Propagation:

*Type cuttings*.—Vegetative meristems having at least 1 node.

*Time to initiate roots*.—3-4 days.

*Time to produce a rooted cutting*.—7-10 days.

*Root habit*.—Fibrous.

*Root description*.—Callus forms in 2-3 days; roots initiate in 3-4 days; and roots become highly branched in 7-10 days.

Branches:

*Quantity per plant*.—8.

*Branch color*.—Red, RHS N186C.

*Texture*.—Smooth.

*Pubescence*.—Not present.

*Stem description*.—Square-shaped and 0.5-0.6 cm in diameter at the soil line.

*Branch diameter*.—0.4-0.5 cm at the base of a 27 cm long branch.

*Branch length*.—25-29 cm.

*Internode length*.—4-5 cm.

*Anthocyanin*.—Red, RHS N186C.

Leaves:

*Quantity of leaves per branch*.—12-14. Arrangement: Opposite.

*Fragrance*.—Not fragrant.

*Shape*.—Ovate.

*Length*.—10-12 cm.

*Width*.—8-9 cm.

*Apex*.—Broadly acuminate.

*Base*.—Sagitate.

*Margin*.—Lobed.

*Leaf texture* (*both surfaces*).—Smooth.

*Pubescence color* (*both surfaces*).—Not present.

*Venation color*.—Upper surface: Center=Purplish red, RHS 61A. Lower surface: Purplish red, RHS 186B.

*Venation pattern*.—Upper surface: Reticulate. Lower surface: Reticulate.

*Color*.—Immature leaf: Upper surface: Center=Purplish red, RHS 64A; Margin=Green, RHS N138A. Lower surface: Center=Purplish red, RHS 64A; Margin=Purple, RHS N77A.

*Color*.—Mature leaf: Upper surface: Center=Purplish red, RHS 63A; Mid-Center=Yellow, RHS 10B; Margin=Green, RHS N137B. Lower surface: Center=Purplish red, RHS 186B; Margin=Purple, RHS N77A.

*Petiole length*.—3.5-4.0 cm.

*Petiole diameter*.—0.2-0.3 cm.

*Petiole color*.—Purplish red, RHS 61A.

*Petiole texture*.—Smooth, no pubescence.

Flowers and seeds: Not observed.

Fruit/seed set: Not observed.

Disease and insect resistance: Disease and insect resistance is typical of the species. The most common insect pests observed on this plant in Gainesville, Fla. have been long-tailed or citrus mealybugs (*Pseudococcus* sp.), which occur on older stock plant material held in the greenhouse for over 3-4 months. Impatiens Necrotic Spot Virus (*Bunyaviridae*) has also been observed in plants confined in greenhouses with mixed crops (peppers) infected with Western flower thrips (*Frankliniella occidentalis*). The most common pathogen of this species in the U.S. is downy mildew (*Peronospora lamii*), and this pathogen has been observed in stock materials grown closely together during the cooler growing seasons.

What is claimed is:

1. A new and distinct *Plectranthus scutellarioides* plant called 'UF15-20-6' as shown and described herein.

* * * * *